United States Patent
Miwa

(10) Patent No.: US 6,299,305 B1
(45) Date of Patent: Oct. 9, 2001

(54) OPHTHALMIC APPARATUS

(75) Inventor: Tetsuyuki Miwa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/504,878

(22) Filed: Feb. 16, 2000

(30) Foreign Application Priority Data

Feb. 18, 1999 (JP) .................................................. 11-039382

(51) Int. Cl.⁷ ...................................................... A61B 3/00
(52) U.S. Cl. ........................... 351/200; 600/307; 604/294
(58) Field of Search ................... 351/200, 202, 351/210, 221, 246; 604/290, 294; 600/307, 318, 321, 383; 514/912; 424/78.04; 128/898

(56) References Cited

U.S. PATENT DOCUMENTS

| | | |
|---|---|---|
| 4,747,683 | 5/1988 | Doane . |
| 5,807,273 | 9/1998 | Suzuki . |
| 6,159,189 * | 12/2000 | Finnemore et al. .................. 604/294 |

FOREIGN PATENT DOCUMENTS

| | | |
|---|---|---|
| 0 232 986 | 8/1987 | (EP) . |
| 7-39519 | 2/1995 | (JP) . |
| 7-136120 | 5/1995 | (JP) . |
| 9-201334 | 8/1997 | (JP) . |
| WO 88/10089 | 12/1988 | (WO) . |

OTHER PUBLICATIONS

Benedetto, D.A., et al., "The instilled fluid dynamics and surface chemistry of polymers in the preocular tear film," XP–002136393, p. 887, Mar. 13, 1975.

* cited by examiner

*Primary Examiner*—George Manuel
(74) *Attorney, Agent, or Firm*—Finnegan, Henderson, Farabow, Garrett & Dunner, L.L.P.

(57) ABSTRACT

An ophthalmic apparatus for measuring dryness of a cornea of an eye to be examined, the apparatus comprising a projecting optical system including a light source for projecting measurement light onto the cornea, a detecting optical system including a photodetector for detecting reflected light from a tear film by projecting the measurement light, an arithmetic device for measuring time-varying changes in the dryness of a predetermined measurement region based on a result detected by the photodetector, and an output device for outputting a measurement result obtained by the arithmetic device.

18 Claims, 5 Drawing Sheets

F I G. 3
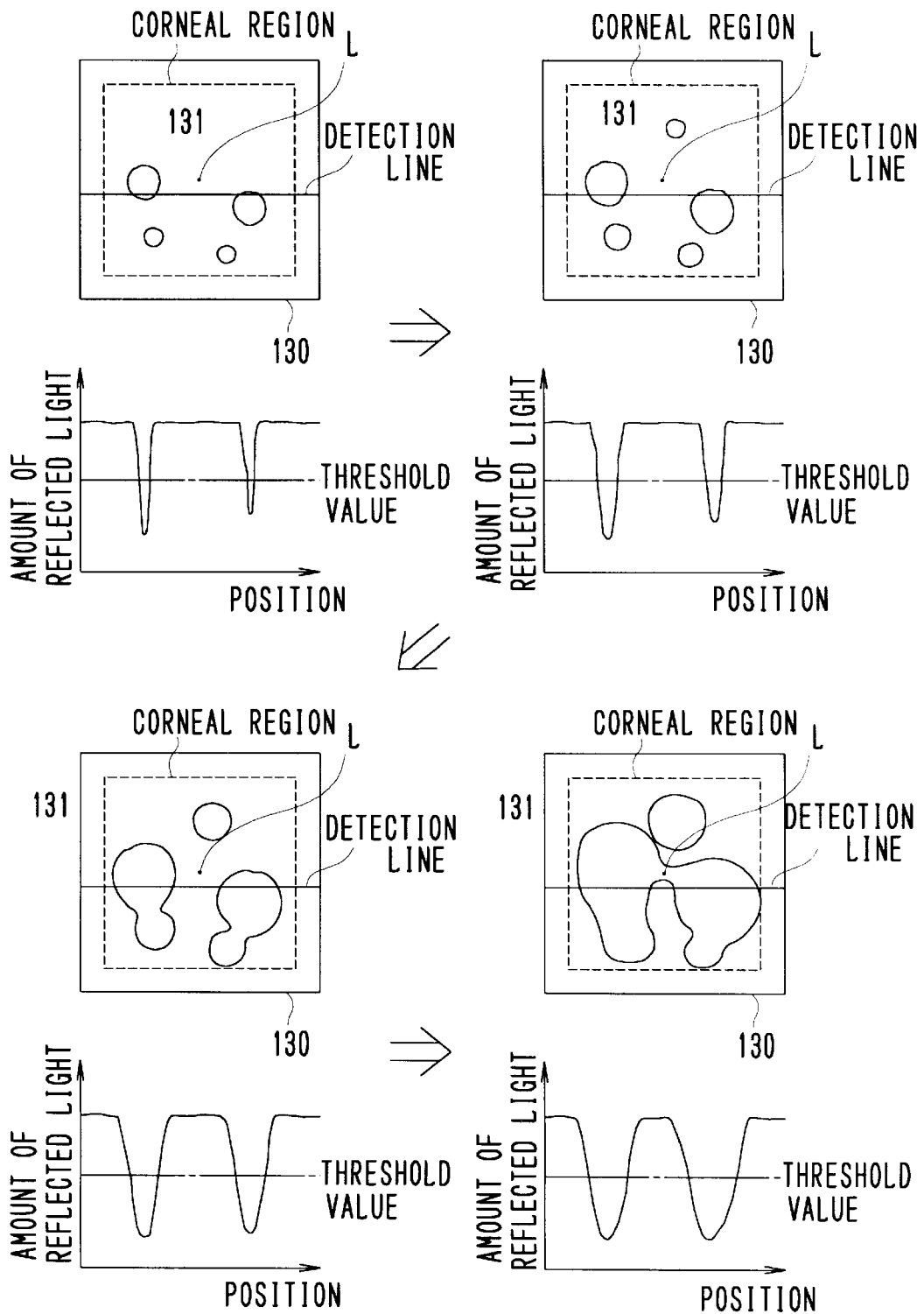

OPHTHALMIC APPARATUS

BACKGROUND OF THE INVENTION

1. Field of the Invention

The present invention relates to an ophthalmic apparatus, and more particularly to an ophthalmic apparatus for measuring dryness of a cornea or a conjunctiva of an eye to be examined.

2. Description of Related Art

Right after blinking, a cornea of an eye is covered with a tear film of almost even thickness. This tear film, however, gradually breaks up (drys out), as the eye remains open. It is important to measure the time taken for the breakup (hereinafter, referred to as BUT (Breakup Time)) in order to detect a defect in the tear film. Besides an aqueous layer, the tear film consists of an oil layer on the outermost surface and a mucin layer on the side of the cornea. The aqueous layer is sandwiched between the two layers. The oil layer has a function of protecting moisture from evaporating and the mucin layer has a function of moisten the corneal surface uniformly. To examine a dry eye caused by reduction of moisture (tear deficiency such as Sjogren's syndrome) or by reduction of the mucin layer (Stevens-Johnson syndrome and the like), the BUT measurement is considered to be extremely important.

Conventionally, diagnosis of such a dry eye has been carried out as follows: first fluorescein, which is a fluorescent material, is applied to an eye to be examined, and then the eye is visually observed under a slit lump until it reaches predetermined dryness thereby measuring the BUT mentioned above.

However, in the BUT measurement as described above, dryness of a corneal surface is measured through observing development of dry spots on the corneal surface by an examiner based on his subjective judgement. Naturally, a different examiner leads to a different measurement result and the accuracy of the measurement depends on the examiner's experience. In addition there are other problems. One example is that it is extremely difficult to judge the dryness in the case where dry spots appear non uniformly.

SUMMARY OF THE INVENTION

The present invention has been made in view of the above circumstances and has an object to overcome the above problems and to provide an ophthalmic apparatus for measuring dryness of a cornea or of a conjunctiva objectively so that highly reliable measurement results can be obtained easily without depending on an examiner's experience.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus for measuring dryness of a cornea of an eye to be examined, the apparatus comprises a projecting optical system including a light source for projecting measurement light onto the cornea, a detecting optical system including a photodetector for detecting reflected light from a tear film by projecting the measurement light, arithmetic means for measuring time-varying changes in the dryness of a predetermined measurement region based on a result detected by the photodetector, and output means for outputting a measurement result obtained by the arithmetic means.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 3 is a view illustrating dry spot detection performed over time based on difference in an amount of reflected light;

DETAILED DESCRIPTION OF THE PREFERRED EMBODIMENTS

Figure 1:
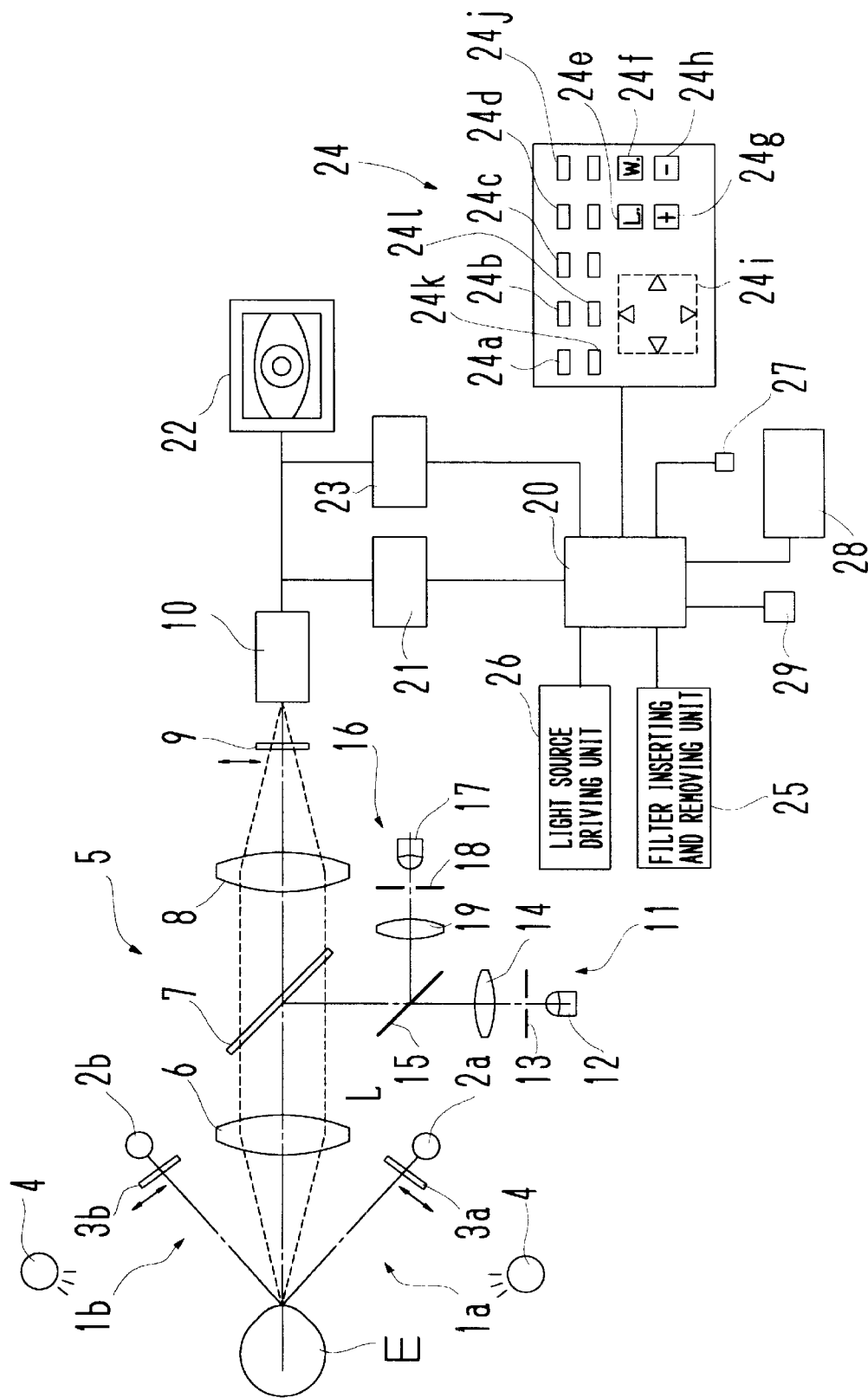
FIG. 1 is a view showing a schematic configuration of an optical system and a control system of an ophthalmic apparatus according to the present invention.

A detailed description of one preferred embodiment of an ophthalmic apparatus embodying the present invention will now be given referring to the accompanying drawings. FIG. 1 is a view showing a schematic configuration of an optical system and an control system of the ophthalmic apparatus according to the present invention.

Reference numeral 1a and 1b are measurement light projecting optical systems for projecting measurement light onto an anterior segment of an eye E to be examined. The two measurement light projecting optical systems are arranged so that each of them projects the measurement light to the eye E obliquely from either right or left. In addition, the measurement light projecting optical systems 1a and 1b respectively comprise halogen lamps 2a and 2b, which emit white illumination light, and fluorescence excitation filters 3a and 3b,which transmit light having a short wavelength within the visible region. The fluorescence excitation filters 3a and 3b can be inserted into, or removed from, an optical path selectively. In addition, the measurement light projecting optical systems 1a and 1b are controlled through operating switches arranged in a switch input unit 24, which will be described later, so as to change the amount of light that the lamps 2a and 2b project, illuminate only one of the lamps 2a and 2b, insert only one of the filters 3a and 3b into the optical path or the like. As the result, selective illumination may be achieved. In addition, the measurement light projecting optical systems 1a and 1b may be configured to make projecting angles of the measurement light variable.

5 is an observation optical system for observing an anterior segment of the eye E. This observation optical system 5 also functions as a detecting optical system for detecting dry spots by receiving light reflected from a cornea or from a conjunctiva of the eye E. Arranged along the optical axis L of the observation optical system 5 are: an objective lens 6; a half mirror 7; an image forming lens 8; a fluorescence filter 9, which can be inserted into, or removed from, the optical path selectively; and a CCD camera 10, which is an area sensor. The fluorescence filter 9 transmits fluorescence within a specific part of visible region but cuts the aforementioned measurement light that is excitation light for fluorescence (the light that has passed the filters 3a or 3b).

11 is an alignment light projecting optical system. Near infrared light emitted from a near infrared LED 12, which is provided as an alignment light source illuminates an aperture 13. Thereafter, the light from the aperture 13 passes through a lens 14 and a beam splitter 15 and is reflected by the half mirror 7. Having been made approximately parallel by the lens 6, the light is finally projected onto the eye E. 16 is a fixation optical system. Visible light emitted form a visible LED 17, which is provided as a fixation light source illuminates a fixation target 18. The light from a fixation target 18 is projected onto a fundus of the eye E via a lens 19, the beam splitter 15, the half mirror 7 and the lens 6. 4 are illumination lamps for illuminating anterior segment of the eye E. An image of the anterior segment of the eye E illuminated by the lamps 4 is photographed by the camera 10 via the lens 6, the half mirror 7 and the lens 8 (at this time, the filter 9 is not inserted into the optical path).

Picture signals that the camera 10 outputs are then inputted to a color TV monitor, the monitor displays the image of the anterior segment of the eye E. Also, the picture signals from the camera 10 are inputted to a picture signal memory 21. From the information stored in this memory 21, an arithmetic control unit 20 detects dry spots appear on the cornea or conjunctiva, and obtains information on change with time in the dry spots (this will be described later in detail). The information on the time-varying dry spots and the results of the BUT measurement obtained by the arithmetic control unit 20 are displayed on the monitor 22 via a graphic information generating unit 23. The graphic information generating unit 23 generates a reticle used in alignment as well as graphics indicating the measurement results according to instructions given by the arithmetic control unit 20.

25 is a filter inserting and removing mechanism unit for inserting the filters 3a and 3b into, or removing the same from the optical path. 26 is a light source driving mechanism unit for driving lightning of the light sources 2a, 2b, 12, 17 and 4. 24 is the switch input unit comprising various switches, each of which is connected to the arithmetic control unit 20.

Figure 2:
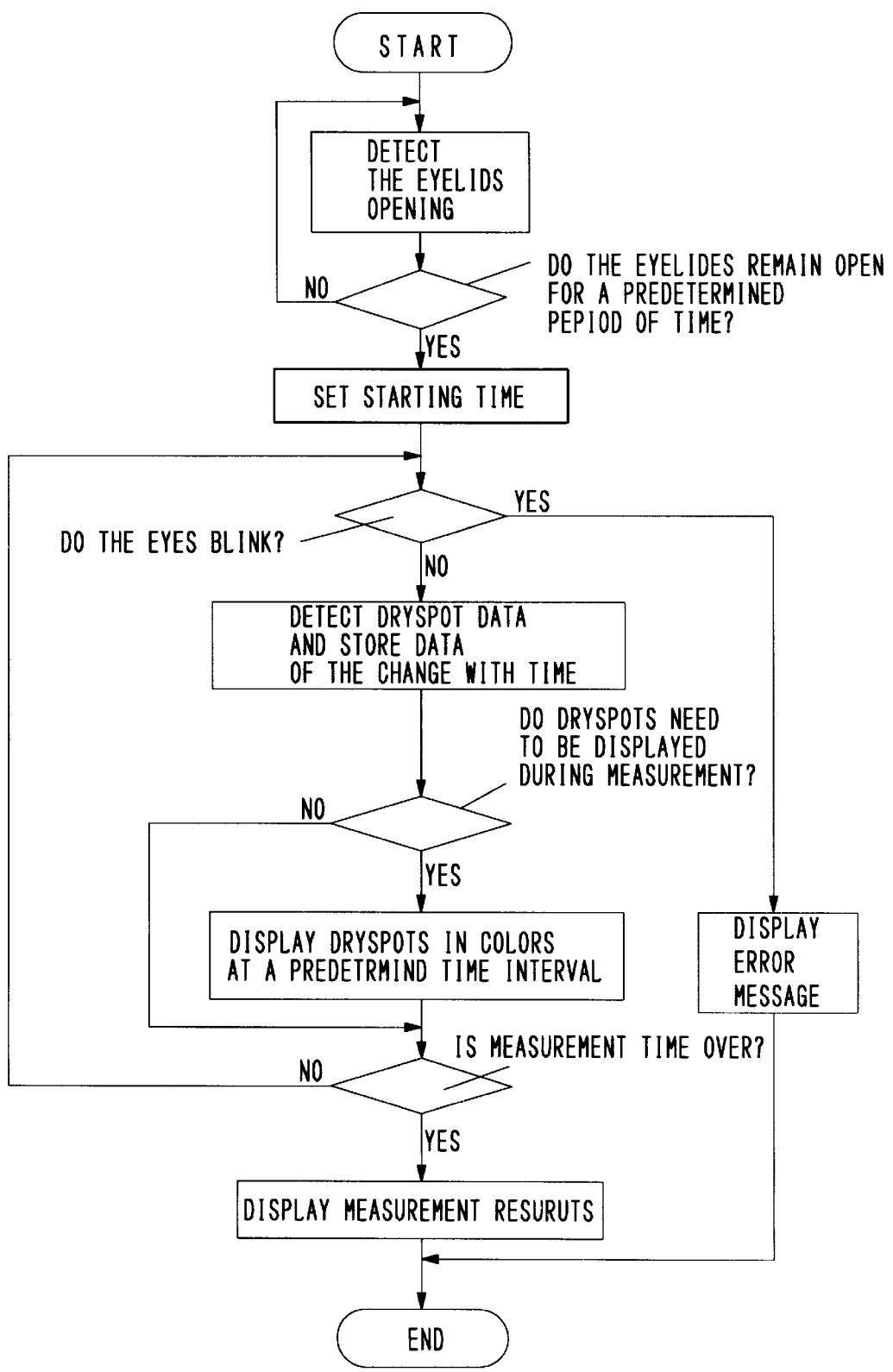
FIG. 2 is a flowchart showing the steps of the dry spot measurement by the ophthalmic apparatus according to the present invention.

Hereinafter, operations of the ophthalmic apparatus having a configuration as above will be described with reference to FIG. 2. Here, the measurement is made after dropping fluorescein into the eye E with the filters 3a, 3b and 9 inserted into the optical path. In this case, in addition, a mode that starts the measurement automatically is selected with a switch 24a arranged in the input unit 24, although the measurement may alternately be started at a push of a measurement starting switch 27.

First, the eye E is positioned at a predetermined position relative to the apparatus, and the eye E is made fixated to the light from the fixation target 18. An image of the anterior segment of the eye E illuminated by the lamps 4 and luminance points for alignment illuminated by LED 12 are displayed on the monitor 22. While observing the examiner aligns the optical systems with the eye E using a conventionally known mechanism, which is not illustrated, such as a joystick (at this time, the filter 9 is not inserted into the optical path). At a press of a switch 24b, after the alignment is completed, the arithmetic control unit 20 lights the lamps 2a and 2b (the filters 3a, 3b and 9 have been inserted into the optical path by this time at a press of a switch 24c after the completion of the alignment). At the same time, the lamps 4 and the LED 12 are tuned off. Then, fluorescein is dropped into the eye E and an examine is instructed to make a blink action to spread out the fluorescein all over the tear film of the eye E.

When the lamps 2a and 2b are lighted, the measurement light passes through the filters 3a and 3b and is projected onto the eye E in a state of excitation. As the result, fluorescence light reflected by the fluorescein being spread over the tear film is detected by the camera 10. The picture signals from the camera 10 are inputted to the memory 21 sequentially, and the arithmetic control unit 20 detects that the eyelids are open whereby starting the measurement automatically. That is to say, the amount of light reflected form the eye E increases as the eyelids open compared to when the eyelids are close. This change (difference) in the amount of reflected light allows to detect whether the eyelids are open. It is also possible to detect whether the eyelids are open from the size of the cornea or of the iris that can be obtained through image processing. Since the eye E may blink a plurality of times, only when the eyelids remain open without blinking for longer than a predetermined period of time, the time that the eyelids open is designated as starting time of the measurement. For detecting whether the eyelids are open, other conventional techniques (one example is disclosed in U.S. Pat. No. 5,807,273, which corresponds to JP publication No. HEI 9-149884) may be applied.

After the measurement is started, the arithmetic control unit 20 detects development of dry spots from difference in the amount of light reflected from the eye E based on the picture signals inputted from the camera 10, and obtains the change with time in the dry spots. FIG. 3 is a view illustrating the dry spot detection performed over time based on difference in an amount of reflected light (one of the detection lines of the camera 10 is illustrated). The tear film covering the corneal surface gradually thins out as the eyelids remain open, and the part where the tear film drys out appears as a dry spot. The amount of the reflected light from the dry spot is extremely small compare to that from the tear film. Thus, if a threshold value is set to the amount of reflected light or to the degree of difference in the amount of the reflected light, the region (area) of the dry spots can be detected. One example of measurement results to indicate the dryness is data about the ratio of the dry spot area 131 to a predetermined corneal region (the size and the position of the corneal region are determined with reference to the alignment position (the optical axis L) along the detection surface 130 of the camera 10 stored in the memory 21). The arithmetic control unit 20 stores this data of ratio repeatedly at a predetermined time interval. When the measurement time (ten seconds in this embodiment) is over, the arithmetic control unit 20 informs the examiner with sound or display that the measurement is terminated, and terminates the measurement automatically.

In the case that the eye E blinks during the above measurement, the amount of the reflected light from the eye E changes drastically. The arithmetic control unit 20 detects a blinking action of the eye E from that drastic change. When a blinking action is detected, a measurement error is displayed on the monitor 22.

Figure 4:
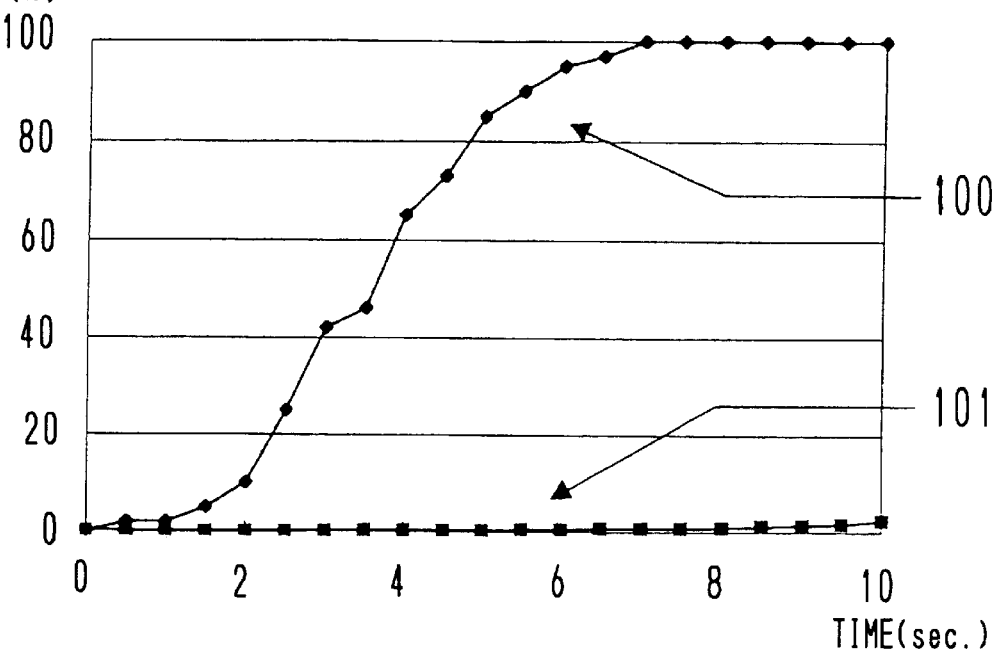
FIG. 4 is a view showing an example displaying measurement results.

After the measurement is terminated, the monitor displays the measurement results. FIG. 4 is a view showing an example displaying the measurement results. Here, the relative area of the dry spots to the measurement area is displayed in a graph in time sequence. A graph 100 is an example showing a case where the eye is a dry eye, while a graph 101 is an example showing a case where the eye is normal.

Incidentally, a level of the threshold value for determining the dry spots may be changed using a switch 24j, which allows the setting to suit a condition of each eye to be examined individually. The level of the threshold value is stored in memory provided in the arithmetic control unit 20 together with the measurement results, and printed out from a printer 28 also together with the measurement results. This allows to carry out measurement at a later date under the same setting in order to observe the progress.

In addition, measurement of dry spots is sensible to its environment for the measurement, especially to the humidity. Thus, it is desirable to make correction to the level of the threshold value for determining dry spots or to the measurement results in view of results of the detection by a humidity sensor 29. For example, when the arithmetic control unit 20 judges from the results detected by the sensor 29 that the humidity in the environment surrounding the apparatus is lower than a predetermined reference value, the level of the threshold value is lowered on the prediction that the corneal surface drys out more quickly than when the humidity is at the reference value. Such correction insures higher accuracy of the measurement.

Figure 5:
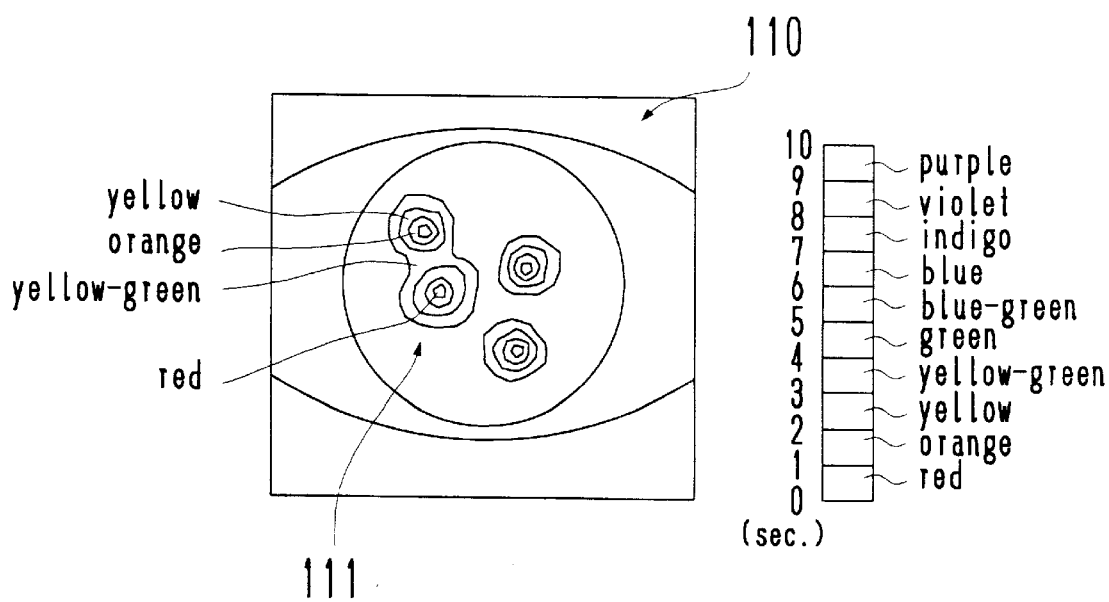
FIG. 5 is a view showing an example displaying time-varying dry spot areas in different colors.

On the monitor 22, as shown in FIG. 5, the detected dry spot areas are displayed in colors and in superposed relation with the image of the eye E at a predetermined time interval. To this end, a mode for this procedure is selected with a switch 24k arranged in the input unit 24. In FIG. 5, contour FIGS. 111 indicate time-varying dry spot areas at each predetermined time interval and the colors indicate the change with time. Such display during the measurement makes it easier to understand the change with time in the dry spots. The time interval for color displaying the contour FIGS. 111 (in the case of this embodiment, one second) may be changed by selecting appropriate time interval using a switch 24l arranged in the input unit 24. In addition, through saving the final display at the completion of the measurement and switching the final display with the display of the measurement results shown in FIG. 4, the change of the dry spots can be grasped visually with ease.

In addition, the measurement results indicating change with time, as FIG. 5 may be stored in an internal or an external storage device. Then, for example, pre-treatment condition and after-treatment condition may be displayed next to each other on the same display screen of the monitor 22 (or on another display device). This makes it easy to observe the development of the change.

Figure 6:
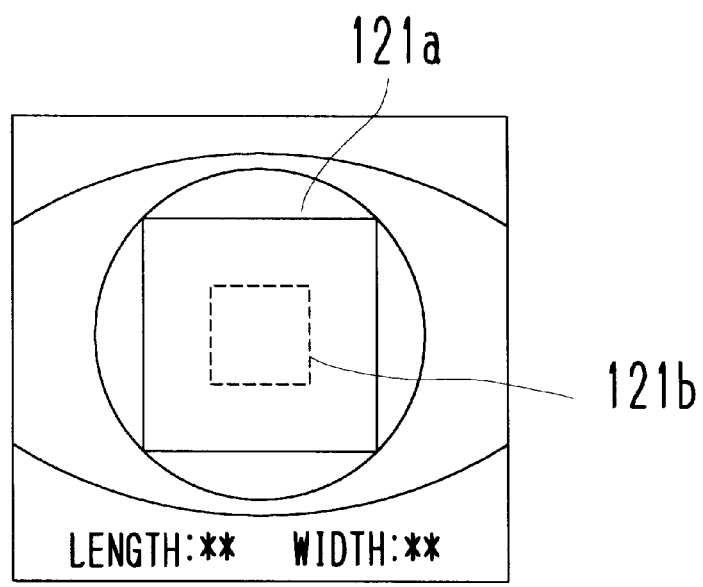
FIG. 6 is a view showing the measurement area setting change.

In the above description, data about ratio of the dry spot area to the predetermined corneal region (relative area) is obtained. However, it is also possible to obtain data about the ratio of the dry spot area to an arbitrary set measurement area. The setting of the measurement area is changed in the following way: first, the area setting change mode is selected using a switch 24d in the input unit 24, the current measurement area as shown by the FIG. 121a in FIG. 6 is displayed on the monitor 22, then parameters of the width and length of the area are changed to those of an intended size using switches 24e, 24f, 24g and 24h. As the result, the size of the measurement area changes as shown by the FIG. 121b in FIG. 6. Thereafter, the area is moved to an intended portion using the switches 24i, which are move keys, then the area setting change mode is released at a push the switch 24d thereby completing the registration of the new setting. To make this change, the image of the anterior segment of the eye E upon the measurement is once stored in the picture memory and the setting is changed on the displayed image so that the change may be made in agreement with the eye E.

Further, the measurement to detect dryness of the corneal surface as described above may be made without fluorescein instillation but with the reflected light from the eye E illuminated by white illumination light from the lamps 2a and 2b (through measuring change in time-varying interference fringes between reflected light from the outermost surface and from the innermost surface of the tear film). In this case, the filters 3a, 3b and 9 are removed from the optical path. In addition, to obtain more selectable interference fringes, polarizing filters may be inserted into the optical path instead of the filters 3a, 3b and 9.

Just as the case of measurement with fluorescein instillation, alignment the eye E is made with the apparatus and white illumination light is projected onto the eye E by the lamps 2a and 2b. Thereafter, the interference fringes are photographed with the camera 10. Based on the level of the reflected light of this photographed interference fringes, change in the amount of reflected light is measured over time until dry spots appear. Unlike fluorescence reflected light due to fluorescein instillation, the amount of reflected light from the interference fringes is closer to that of in a natural state. Since development of dry spots may be observed while observing the interference fringes, diagnosis may be made based on the change with time both in the interference fringes and in the dry spots. Such modifications are included in the present invention within the scope derived from the same technical idea.

Figure 7:
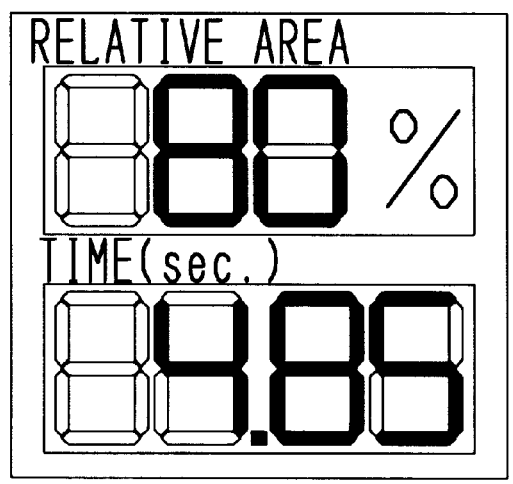
FIG. 7 is a view showing an example displaying measurement results.

In addition, one alternative to the display of the time-varying relative area of the dry spots area to the measurement area as shown in FIG. 4 is display of the time required for the relative area to have a predetermined ratio (namely BUT) as shown in FIG. 7 (FIG. 7 shows that that BUT is 4.85 second at the moment the ratio of the dry spot area relative to the measurement area is 80%).

Further, instead of obtaining the ratio of the dry spot area relative to the measurement area, the dryness may be judged based on the degree of the reduction in the amount of reflected light in the overall measurement area relative to the reference value. That is, a comparison is made between the reference value and an amount of the reflected light at a predetermined time interval to obtain difference therebetween. Larger difference is regarded to indicate a larger dry spot area. If the relationship between the difference in the amount of light and the ratio (the relative area) of dry spot area is empirically obtained and stored beforehand, change in the time-varying dry spot area may be displayed. Here, the reference value is determined by the amount of reflected light stored in the memory provided in the arithmetic control unit 20 upon starting the measurement (upon detecting the eyelids opening condition). This technique is useful within a limited measurement area to some extent. Consequently, a measurement area should be set to be of an arbitrary-size in the aforementioned manner beforehand.

As described above, according to the present invention, dryness of the cornea or the conjunctiva may be measured objectively without depending on the examiner's subjective judgement. Thus, highly reliable measurement results can be obtained quantitatively.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for measuring dryness of a cornea of an eye to be examined, the apparatus comprising:
    a projecting optical system including a light source for projecting measurement light onto the cornea;
    a detecting optical system including a photodetector for detecting reflected light from a tear film by projecting the measurement light;
    arithmetic means for measuring time-varying changes in the dryness of a predetermined measurement region based on a result detected by the photodetector; and
    output means for outputting a measurement result obtained by the arithmetic means.

2. The ophthalmic apparatus according to claim 1, wherein the arithmetic means obtains time-varying changes of a area occupied by a dried region relative to the predetermined measurement region based on an amount of the reflected light detected by the photodetector.

3. The ophthalmic apparatus according to claim 2, further comprising time setting means for setting measurement time, and
    wherein the arithmetic means obtains the time-varying changes in the area occupied by the dried region within the set measurement time.

4. The ophthalmic apparatus according to claim 2, further comprising area setting means for setting a size of the area occupied by the dried region, and
    wherein the arithmetic means measures the time required for the area occupied by the dried region to reach the set size based on the time-varying changes therein.

5. The ophthalmic apparatus according to claim 2, further comprising threshold setting means for setting a threshold value of the amount of the reflected light.

6. The ophthalmic apparatus according to claim 5, further comprising storage means for storing the set threshold value together with the measurement result.

7. The ophthalmic apparatus according to claim 1, wherein the arithmetic means obtains the time-varying changes in the dryness from a degree of reduction in the amount of the reflected light from the predetermined measurement region based on an amount the reflected light detected by the photodetector.

8. The ophthalmic apparatus according to claim 7, further comprising storage means for storing the amount of the reflected light from the predetermined measurement region at the time of starting the measurement as a reference value, and
    wherein the arithmetic means obtains the time-varying changes in a dried region from difference in the amount of light between the detected reflected light and the stored reference value.

9. The ophthalmic apparatus according to claim 1, further comprising range setting means for setting the measurement region.

10. The ophthalmic apparatus according to claim 1, wherein the projecting optical system includes a fluorescence excitation filter that transmits only part of the light from the light source including a wavelength that excites fluorescent material applied to the eye selectively, and
    the detecting optical system includes a fluorescent filter that transmits the excited fluorescence selectively.

11. The ophthalmic apparatus according to claim 1, wherein the projecting optical system includes a first polarizing filter that transmits the light from the light source selectively, and
    the detecting optical system includes a second polarizing filter that only transmits reflected light of the light having passed through the first polarizing filter selectively.

12. The ophthalmic apparatus according to claim 1, further comprising eyelid-opening detecting means for detecting an eyelid-opening condition of the eye.

13. The ophthalmic apparatus according to claim 12, the eyelid-opening detecting means detects the eyelid-opening condition based on difference in the amount of reflected light detected by the photodetector.

14. The ophthalmic apparatus according to claim 12, further comprising measurement control means for controlling the measurement based on the eyelid-opening condition detected by the eyelid-opening detecting means.

15. The ophthalmic apparatus according to claim 12, wherein the arithmetic means determines the time that the eyelid-opening detecting means detects a predetermined eyelid-opening condition as measurement starting time.

16. The ophthalmic apparatus according to claim 1, wherein the output means includes display means for graphically displaying an image of an anterior segment of the eye and the time-varying changes of the dryness in superposed relation.

17. The ophthalmic apparatus according to claim 1, further comprising correction means for correcting the measurement result or a measurement standard depending on a state of environment for the measurement.

18. The ophthalmic apparatus according to claim 17, further comprising a humidity sensor for detecting humidity surrounding the apparatus, and
    wherein the correcting means corrects the measurement result or the measurement standard based on a result detected by the humidity censor.

* * * * *